(12) United States Patent  (10) Patent No.: US 7,060,258 B2
Li  (45) Date of Patent: Jun. 13, 2006

(54) METHOD OF MAKING ALUMINUM-ZIRCONIUM ANTIPERSPIRANT OF ENHANCED EFFICACY

(75) Inventor: Zijun Li, Westfield, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 332 days.

(21) Appl. No.: 10/756,620

(22) Filed: Feb. 17, 2004

(65) Prior Publication Data

US 2005/0180934 A1 Aug. 18, 2005

(51) Int. Cl.
*A61K 8/00* (2006.01)
*A61K 8/02* (2006.01)
*A61Q 15/00* (2006.01)

(52) U.S. Cl. .............. 424/65; 424/66; 424/68; 424/400; 424/401

(58) Field of Classification Search .............. 424/65, 424/66, 68, 400, 401
See application file for complete search history.

(56) References Cited

U.S. PATENT DOCUMENTS

| 4,775,528 A | 10/1988 | Callaghan et al. |
| 4,871,525 A | 10/1989 | Giovanniello et al. |
| 6,375,937 B1 | 4/2002 | Chopra et al. |
| 6,436,381 B1 | 8/2002 | Carrillo et al. |

FOREIGN PATENT DOCUMENTS

EP 0653202 A1 5/1995

*Primary Examiner*—Shelley A. Dodson
(74) *Attorney, Agent, or Firm*—Arthur J. Plantamura

(57) ABSTRACT

A novel efficacious and less irritant aluminum-zirconium antiperspirant composition is provided by the addition of a small amount of $AlCl_3$ and/or HCl to the activated aluminum component. After the heating of diluted basic aluminum chlorohydrate solution, cooling to room temperature, mixing with small amount of $AlCl_3$ or HCl and then reacting with zirconium glycine complex, an aluminum-zirconium salt is produced with a maximum amount of depolymerization aluminum and zirconium species. The addition of a small amount of $AlCl_3$ or HCl to the diluted and activated aluminum chlorohydrate solution accelerates the depolymerization of the activated ACH solution, and upon the addition of zirconium glycinate the solution is further depolymerized and results in the formation of less polymerized zirconium species.

11 Claims, 2 Drawing Sheets

METHOD OF MAKING ALUMINUM-ZIRCONIUM ANTIPERSPIRANT OF ENHANCED EFFICACY

This invention relates to a method of making solid aluminum-zirconium antiperspirant by the addition of small amount of $AlCl_3$ and/or HCl to the activated aluminum component, followed by the mixing with a zirconium glycine complex and drying the solution mixture to a powder. The novel aluminum-zirconium (Al—Zr) composition has a metal (Al+Zr) to chloride molar ratio of about 1.20 to about 1.30; a HPLC Band IV of at least about 20%, but less than about 25%; and at least 10% aluminum present at chemical shift ($\delta$) of about 0 ppm and at least 2% aluminum present at chemical shift of about 63 ppm by $^{27}Al$ NMR.

BACKGROUND OF THE INVENTION

Aluminum-zirconium compounds are well known as effective antiperspirants. The presence of zirconium species increases the efficacy of aluminum-zirconium antiperspirant by the depolymerization of aluminum species. This depolymerization is more important when activated aluminum antiperspirant solution is involved. However, zirconium species become further polymerized during the process.

U.S. Pat. No. 4,775,528 describes a solid aluminum-zirconium antiperspirant salt having HPLC peak height of peak 4 (or Band III) to that of peak 3 (or Band II) is at least 2. The method of making the antiperspirant of that patent involves mixing activated (HPLC peak 4 to peak 3 area ratio of at least 0:5) aluminum chlorohydrate solution with zirconyl hydroxy chloride solution at a temperature of at least 50° C. and quickly drying the solution.

U.S. Pat. No. 4,871,525 discloses aluminum-zirconium hydroxy halide glycinate complex having a peak height ratio of peak 4 to peak 3 of 0.5 to 1.8 and wherein peak (1+2) contains less than 4% of the polymer distribution by weight. The aluminum component is made by direct reaction of aluminum metal with $AlCl_3$ or HCl at about 8–35% weight to weight concentration. The aluminum component, zirconyl hydroxy chloride and glycine of that solution are maintained at 50°–100° C. for a period of time. The solution is then dried.

Both U.S. Pat. No. 4,775,528 and U.S. Pat. No. 4,871,525 are silent regarding peak 5 (or Band IV) and apparently do not recognize the significance of maintaining control of the limits of the corresponding aluminum-zirconium antiperspirant. Also the processes of both patents polymerize the zirconium species to a greater extent because of the higher temperature treatment, which is believed to reduce the efficacy of the corresponding aluminum-zirconium antiperspirant salt.

European Patent 0 653 203 A1 teaches a process of making an antiperspirant active said to have an enhanced efficacy. The active is prepared by the reaction of activated aluminum component with zirconium complex. The zirconium sources are chosen to be the least polymerized so that depolymerized zirconium species are obtained in the final product. That reference, also, evidences no recognition of the distribution of aluminum species such as aluminum monomers and dimers or Band IV species, which is believed to be critical for the efficacy of aluminum-zirconium antiperspirant.

U.S. Pat. No. 6,375,937 describes aluminum-zirconium salts having metal to chloride molar ratio of about 0.9–1.2, and a glycine to zirconium molar ratio of greater than 1.3 while U.S. Pat. No. 6,436,381 relates to aluminum-zirconium antiperspirant salts with high peak 5 aluminum content of at least 33% wherein the antiperspirant salts have metal to chloride ratio of about 0.9–1.0.

Aluminum-zirconium antiperspirant with low M/Cl ratio such as those described in U.S. Pat. Nos. 6,375,937 and 6,436,381 tend to be more irritating to the skin than the corresponding salt with higher ratio. As a consequence, there is a tendency to add more amino acid in order to minimize the irritancy, and in turn this tends to reduce the efficacy of the aluminum-zirconium antiperspirant.

It is highly desirable to make an activated aluminum-zirconium salt, which is not an irritant to the skin and has enhanced efficacy. In accordance with the present invention it has been discovered that a novel activated aluminum-zirconium composition having a M/Cl ratio of about 1.20 to about 1.30 can be made in the presence of small amount of $AlCl_3$ or HCl to have a maximum amount of depolymerized aluminum and zirconium species, and provides an antiperspirant that has enhanced efficacy and has a marked reduction in skin irritancy.

The activated aluminum-zirconium salts generally have characteristic HPLC Band III/II area ratio of at least 0.5, usually at least 1 with at least 80% aluminum is in Band III and II. There is no requirement on Band IV (or peak 5). In order to have the above HPLC profile, diluted aluminum-zirconium antiperspirant solutions are produced and dried. It is known in the art that that such diluted Al/Zr solution is very unstable. On aging the percentage of Band III decreases and the percentage of Band II increases. No study is known that reports on aging the changes in Band IV that consists of aluminum monomers and dimers. It has been only recently that higher a Band IV has been attributed to a higher efficacy of aluminum-zirconium antiperspirant, reference U.S. Pat. No. 6,436,381. On aging HPLC Band IV usually doesn't decrease. $^{27}Al$ NMR, which reveals the structures of the aluminum species indicates that the amount of Al monomer decreases on aging as can be seen by references to Example 3 herein below. In accordance with the invention I have found that aluminum monomers and dimers generated in the activated aluminum-zirconium salt solutions are very sensitive to the reaction conditions. Different amount of aluminum monomers, dimers and polymers are produced under different reaction conditions and that is believed to affect the efficacy of the activated aluminum-zirconium salt. The changes in the structures of aluminum under different reaction conditions sometimes can only be observed using $^{27}Al$ NMR, not by HPLC size exclusion chromatograph.

SUMMARY OF THE INVENTION

The present invention relates to a method of making solid activated aluminum-zirconium composition having metal to chloride ratio of about 1.20 to about 1.30. The antiperspirant salt has an HPLC Band IV of at least about 20% or more, but less than about 25%, and a Band III to Band II area ratio of about 1 or higher. The active aluminum-zirconium salt of the invention has at least 10% aluminum at chemical shift of about 0 ppm and at least 2% aluminum at chemical shift of about 63 ppm by $^{27}Al$ NMR. In obtaining the requisite activated aluminum-zirconium salt of the invention a small amount of $AlCl_3$ or HCl or a mixture thereof is added to the antiperspirant salt during the reaction while carefully controlling the reaction conditions such that the antiperspirant salt prepared has maximum depolymerized aluminum and zirconium species resulting in a product characteristic, which offers higher efficacy and avoids skin irritancy.

DETAILED DESCRIPTION OF THE INVENTION

Figure 1:
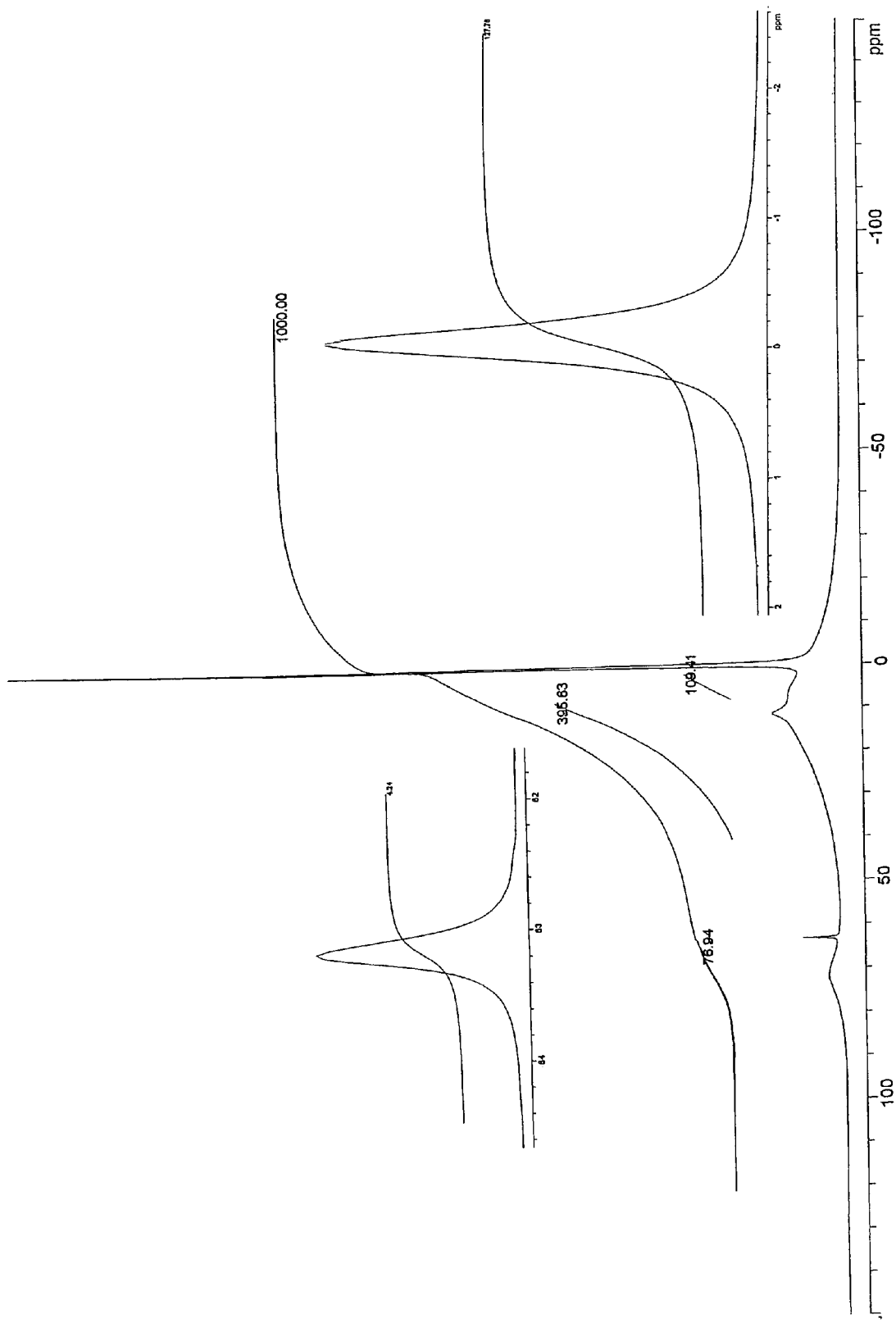
FIG. 1 is an $^{27}$Al NMR chromatogram of a powder according to the present invention.
Figure 2:
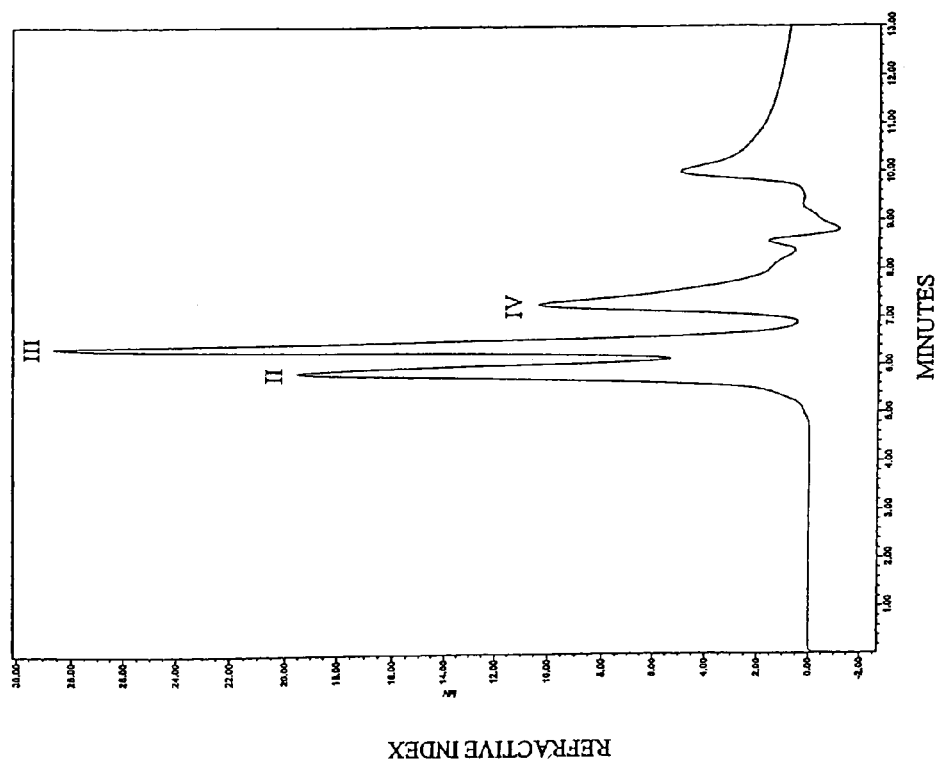
FIG. 2 is a HPLC chromatogram of another powder obtained according to the present invention.

Preparation of the activated aluminum-zirconium antiperspirant salt of the invention is initiated by heating a concentration of about 8 to about 20% by weight basic aluminum halides and nitrate of the formula:

wherein X is Cl, Br or NO$_3$, wherein a is from about 1 to about 1.5 to from about 50° C. to about reflux for about 2 to 20 hrs, cooling to RT, mixing with a small amount of AlCl$_3$ or HCl or a mixture thereof, in amounts from the weight ratio of aluminum in basic aluminum halides or nitrate to the weight of AlCl$_3$ (32°Be) of about 0.5 to about 10, preferably from about 1 to about 8 and most preferably from about 3 to about 5 for from about 5 minutes to about 30 minutes, then mixing with zirconium glycine compounds of the formula:

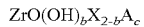

wherein b is a numerical number from 0 to 0.7, X is Cl, Br or NO$_3$, A is an amino acid and c is a number from 0.8 to about 1.2, at RT for no more than one hour, and spray dry the solution.

The zirconium chlorohydroxy glycinate solution is prepared by mixing basic zirconium carbonate with hydrochloric acid or zirconium oxychloride at an elevated temperature and then mixing with glycine at about RT. Preferably the glycine to zirconium molar ratio is about 1.

In present invention reaction conditions have a very significant effect on the polymer distributions of aluminum and zirconium species, which in turn affects the efficacy of the antiperspirant solutions. The effect is especially important for the activated aluminum-zirconium solutions.

According to the present invention, the addition of small amount of AlCl$_3$ or HCl to the activated aluminum component produces a surprising beneficial effect. After the heating of diluted basic aluminum chlorohydrate solution (ACH) and cooling to room temperature, and the introduction and mixing with the AlCl$_3$ or HCl followed by the admixture with the zirconium glycine complex, an aluminum-zirconium salt is produced that possesses a maximum amount of depolymerized aluminum and zirconium species. Not wishing to be bound with any theories, it is believed that the addition of small amount of AlCl$_3$ or HCl to the diluted and activated ACH solution accelerates the depolymerization of the activated ACH solution which, upon the addition of zirconium glycinate solution, results in a further depolymerization. Moreover, the zirconium species also experiences less basic environment which facilitates the formation of less polymerized zirconium species.

It is important that the zirconium chlorohydroxy glycinate solution is added slowly to the activated basic aluminum chloride solution because a rapid addition leads to the random formation of polymers that are relatively much more amenable to further polymerization to higher molecular weight species.

The concentration of activated aluminum solution has an effect on the polymerization of final aluminum-zirconium salt. According to the invention, the more dilute the activated aluminum solution is, the more polymerized zirconium species will be formed in the final salt. However, if the concentration of activated basic aluminum solution is too high, i.e. of a magnitude significantly in excess of 20% by weight or higher, the aluminum species became too difficult to be depolymerized by the zirconium species. Preferably the concentration for activated basic aluminum chlorohydrate solution is about 12% by weight to about 15% by weight.

$^{27}$Al NMR shows that the mixing time of activated aluminum solution and zirconium chlorohydroxy glycinate affect the formation of aluminum monomers and Al$_{13}$ species. The mixing time depends on the concentration of activated aluminum solutions. Certain mixing time is required to generate maximum depolymerized aluminum species while keeping zirconium species at minimum polymerization level. The mixing time also depends on the form of zirconium species. The higher the Cl/Zr ratio of the zirconium solution, the less the mixing time is required. Aging of the activated aluminum-zirconium solution has a substantial impact on the formation of aluminum monomers and the polymerization of zirconium species. Generally speaking the shorter the aging time the higher the amount of aluminum monomers that is produced, and the lesser the zirconium species is polymerized.

The $^{27}$Al NMR also indicates that less aluminum monomers are present in the presence of higher amount of glycine. This may be due to the coordination between aluminum monomers and glycine. In addition it is also observed that there is an increase in the larger aluminum polymer species, such as Al$_{41mer}$. However, when small amount of AlCl$_3$ or HCl is added to the activated aluminum component, the presence of higher amounts of glycine does not produce a reduction in the amount of aluminum monomers and no increase in Al$_{41mer}$ is observed. It is necessary that the amount of glycine be controlled because an amount of glycine which is too low will cause the rapid polymerization of zirconium species such that the final aluminum-zirconium solution will gel quickly, while too much glycine results in a decrease in efficacy. Preferably the amount of glycine is controlled such that the ratio of glycine to zirconium is from about 0.8 to about 1.1.

The degree of the polymerization of aluminum complexes can be determined by a size exclusion column that is connected to the high performance liquid chromatograph (HPLC). The highest molecular weight Al species are eluted first, designated as Band I. Bands II and III designate intermediate molecular weight complexes. Band IV designates the lowest molecular weight Al complexes, including monomers and dimers. The relative area of one or more peak is determined in order to characterize the distribution of polymeric species in the aluminum complexes formed.

A Phenominex Column and a Waters Column connected in series are used to obtain a HPLC chromatograph. A sample of 2% by weight of aluminum is filtered through a 45-micron filter and chromatographed within 15 minutes using a 0.01N nitric acid solution as the mobile phase. The activated aluminum-zirconium antiperspirant salt of the present invention has a HPLC Band IV of about 20% or more, but less than 25%, and Band III/II area ratio of about 1 or higher, preferably about 1.2. $^{27}$Al Nuclear Magnetic Resonance (NMR) is selected to identify the structures of different aluminum species in the activated aluminum-zirconium antiperspirant salt. The antiperspirant salt is generally dissolved in deuteriated water (D$_2$O) to form a 10% by weight solution just before the measurement. Data were collected using a Varian Inova 400 instrument at 104.2 MHz.

Generally a sharp peak at chemical shift of about 0 ppm by $^{27}$Al NMR indicates the presence of octahedral Al monomer and a sharp peak at about 63 ppm indicates the presence of $Al_{13}$ species in which 12 octahedral Al species showing the peaks that are too broad due to the significant electric field gradients at the nuclei which lead to efficient quadrupole relaxation. A broad chemical shift at about 72 ppm is an indication of the presence of $Al_{41}$ species. Higher molecular weight aluminum species generally show chemical shifts that are too broad to be detected. Activated aluminum antiperspirant salt usually consists of $Al_{13}$, $Al_{41}$ species and probably some higher molecular weight aluminum species with very small amount of Al monomers and dimers. Aluminum polymers start to depolymerize to form more monomers and dimers upon addition of zirconium complexes. Zirconium species, however, tend to be further polymerized. As a consequence it is very important to control the conditions of the reaction so the final product will have maximum depolymerized aluminum species and minimum polymerized zirconium species. In accordance with the present invention, it is able to obtain an aluminum-zirconium salt containing from about 10% to about 15% aluminum monomer species while controlling the polymerization of zirconium species at very low level.

EXAMPLE 1

The example illustrates the general procedure for making the novel activated aluminum-zirconium antiperspirant powder of the invention.

500 parts of 50% ACH (12.18% Al, 8.1% Cl) solution, 1192 parts of water were mixed and refluxed for 4 hrs, which was then cooled to RT. To this solution was added 15 parts of $AlCl_3$ (32°Be) in 5 min. This was followed by the addition of 342 parts of zirconium chlorohydroxy glycinate solution (glycine/Zr ratio of 1) to the above solution. The resultant solution was mixed for about 10 min. and was spray dried.

Chemical analysis of the powder is as follows: 14.35% Al, 13.78% Zr, 18.38% Cl and 10.9% Glycine. The powder was dissolved in $D_2O$ to form a 10% by weight solution and immediately run the $^{27}$Al NMR, the spectrum is shown in FIG. 1.

EXAMPLE 2

The example compares the effect of $AlCl_3$ addition on the final activated aluminum-zirconium powder.

The process of the preparation of aluminum-zirconium salt is similar to that of Example 1. 8.3% w/w activated ACH solution was used. In one case, $AlCl_3$ was added whereas no $AlCl_3$ was introduced in another case. The results are listed in Table I

TABLE I

| $AlCl_3$ addition | Al/Cl ratio of 8.3% w/w "ACH" | Cl/Zr ratio of ZHC | M/Cl |  % @ 0 ppm | % @ 63 ppm | % @ 72 ppm |
|---|---|---|---|---|---|---|
| Yes | 1.97 | 1.73 | 1.3 | 11.89 | 0.34 | 8.81 |
| No | 1.96 | 1.79 | 1.3 | 8.70 | 0.205 | 12.15 |

As seen from $^{27}$Al NMR, the addition of small amount of $AlCl_3$ lead to the formation of more depolymerized aluminum species in the final activated aluminum-zirconium powder.

EXAMPLE 3

The example illustrates the effect of aging of diluted aluminum-zirconium solution.

A 12.5% w/w diluted Reach RE 301 solution (Reheis Intermediate Al/Cl ratio of 1.7) was refluxed for 2 hrs, which was cooled to RT. Small amount of $AlCl_3$ (32°Be) was added, followed by the addition of zirconium chlorohydroxy glycinate (Cl/Zr ratio of 1.36 and Glycine/Zr ratio of 1). The solution was aged for 0.5 hrs (S), 3 hrs (M) and 6 hrs (E) respectively at RT and was spray dried. $^{27}$Al NMR spectra were collected for the three powders (10% by weight solution in $D_2O$) and the results are set forth in Table II:

TABLE II

| | Aging Time | 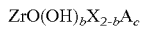 % @0 ppm | % @63 ppm | % @72 ppm |
|---|---|---|---|---|
| S | 0.5 hrs | 11.2 | 0.56 | 9.76 |
| M | 3 hrs | 9.24 | 0.47 | 10.78 |
| E | 6 hrs | 8.87 | 0.094 | 11.17 |

While the invention has been described with reference to the preferred embodiment thereof, it will be appreciated by those skilled in the art that modifications can be made to the apparent variants of the invention without departing from the spirit and scope thereof. Accordingly, the invention is limited only by the scope of the claims.

What is claimed:

1. A method of making solid activated aluminum-zirconium composition having a metal/chloride ratio of about 1.2 to about 1.3 comprising:
   i) heating 8–20% by weight basic aluminum halides or nitrate of the formula:

$Al_2(OH)_{6-a}X_a$ wherein X is Cl, Br or $NO_3$, wherein a is from about 1 to 1.5 from 50° C., to about reflux for about 2 to 20 hours and cooling to RT, mixing with small amount of $AlCl_3$ or HCl or a mixture there of $AlCl_3$ and HCl at about RT for a period of about 5 minutes to about 30 minutes,
   ii) mixing with the solution of a zirconium glycine compound of the formula:

$ZrO(OH)_b X_{2-b} A_c$ wherein b is a numerical number from 0 to 0.7, X is Cl, Br or $NO_3$, A is an amino acid, c is a number from 0.8 to about 1.2 and
   iii) drying the blended solution of (i) and (ii) to a solid.

2. The method according to claim 1 wherein the amount of $AlCl_3$ added is such that the weight ratio of aluminum in basic aluminum halides to the weight of $AlCl_3$ (32°Be) is about 0.5 to about 10.

3. The method according to claim 1 wherein the amount of $AlCl_3$ added is that the weight ratio of aluminum in basic aluminum halides to the weight of $AlCl_3$ (32°Be) is about 3 to about 5.

4. The method according to claim 1 wherein the mixing time of activated aluminum component and $AlCl_3$ is about 1 to about 5 minutes.

5. The method according to claim 1 wherein the mixing time of activated aluminum component and $AlCl_3$ is from about 25 to about 30 minutes.

6. The method according to claim 1 wherein the amino acid is glycine.

7. The method according to claim 1 wherein the molecular ratio of glycine to zirconium is 1.

8. An activated Al–Zr composition having a metal (Al+Zr) to chloride molar ratio of about 1.20 to about 1.30 and aluminum to zirconium atomic ratio of about 2 to 10 with at least 10% Al species at chemical shift about 0 ppm and at least 2% Al species at chemical shift about 63 ppm by $^{27}Al$ NMR.

9. A composition according to claim 8 wherein the composition has about 20% HPLC Band IV.

10. A composition according to claim 8 wherein the composition has a HPLC Band III/II area ratio of about 1.

11. A composition according to claim 8 wherein the composition has amino acid to zirconium mole ratio of about 0.8 to about 1.2.

* * * * *